United States Patent
Salven et al.

(10) Patent No.: US 7,301,166 B2
(45) Date of Patent: Nov. 27, 2007

(54) OPTICAL MULTIPLEXER FOR LIQUID SAMPLES IN A CONDUIT

(75) Inventors: Owe Salven, Uppsala (SE); Stig Tormod, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 202 days.

(21) Appl. No.: 10/538,403

(22) PCT Filed: Dec. 16, 2003

(86) PCT No.: PCT/EP03/14317

§ 371 (c)(1),
(2), (4) Date: Nov. 2, 2005

(87) PCT Pub. No.: WO2004/055567

PCT Pub. Date: Jul. 1, 2004

(65) Prior Publication Data

US 2006/0231780 A1  Oct. 19, 2006

(30) Foreign Application Priority Data

Dec. 17, 2002 (GB) ................ 0229336.3

(51) Int. Cl.
*G01N 15/06* (2006.01)

(52) U.S. Cl. ............... 250/573; 250/239

(58) Field of Classification Search ........... 250/573, 250/575, 576, 221, 239; 422/68.1; 356/246, 356/448; 436/169; 73/53.05, 61.48
See application file for complete search history.

(56) References Cited

U.S. PATENT DOCUMENTS 3,881,826 A   5/1975  De Leeuw
4,306,152 A * 12/1981 Ross et al. ............ 250/343
4,699,457 A  10/1987  Goodman

FOREIGN PATENT DOCUMENTS

| DE | 195 15 375 | 11/1996 |
| EP | 0 601 310 | 6/1994 |
| EP | 0 610 913 | 8/1994 |
| GB | 2 014 305 | 8/1979 |
| GB | 2 251 303 | 7/1992 |
| GB | 2 280 026 | 1/1995 |

* cited by examiner

*Primary Examiner*—Que T Le
(74) *Attorney, Agent, or Firm*—Dwayne L. Bentley; Yonggang Ji

(57) ABSTRACT

Multiplexer for electromagnetic radiation, e.g. UV-light, in which a single electromagnetic radiation source (203) and a single electromagnetic radiation detector (223) are connectable in turn to a plurality of sample-containing units (207(a)-207(n)). The multiplexer comprises a sled (253) movable in relation to a fixed base (255) by an actuator (281).

7 Claims, 3 Drawing Sheets

OPTICAL MULTIPLEXER FOR LIQUID SAMPLES IN A CONDUIT

CROSS REFERENCE TO RELATED APPLICATIONS

This application is a filing under 35 U.S.C. § 371 and claims priority to international patent application number PCT/EP2003/014317 filed Dec. 16, 2003, published on Jul. 1, 2004 as WO 2004/055567 and also claims priority to patent application number 0229336.3 filed in Great Britain on Dec. 17, 2002; the disclosures of which are incorporated herein by reference in their entireties.

FIELD OF THE INVENTION

The present invention relates to devices of the type mentioned in the preambles of the independent claim.

PRIOR ART

In liquid chromatography and other analytical methods, liquids containing analytes are often transported through a tube from a chromatographic column or other device to a collecting device such as a fraction collector. Fraction collectors are devices containing receptacles into which analytes of interest are dispensed and unwanted analytes and buffer solutions are dumped to waste. The presence of an analytes in a sample-containing unit such as a flow cell can be detected by placing a source of electromagnetic radiation e.g. an ultra-violet (UV) light source, on a known position at one end of a conduit in a flow cell, a detector of electromagnetic radiation, e.g. a UV detector, on the opposite end of the UV-transparent conduit and measuring the amount of electromagnetic radiation, e.g. UV light, received by the electromagnetic radiation detector e.g. the UV detector. The amount of electromagnetic radiation, e.g. UV light, detected varies according to the composition of the liquid flowing though the conduit and if the analyte of interest is an electromagnetic radiation, e.g. UV light, absorber then a drop in the amount of radiation, e.g. UV light, detected by the electromagnetic radiation, e.g. UV light, detector signals the presence of the analyte. If the flow rate in cm per second and distance from the position of the detector to the fraction collector are known, then it is a simple matter to calculate how long it will take the analyte to travel from the position where it was detected in the detector to the fraction collector. The results of this calculation can be used to control the fraction collector so that the analyte is dispensed into a receptacle.

Conventionally, each source and corresponding detector of electromagnetic radiation monitors one sample-containing unit. This means that if a plurality of sample-containing unit need to be monitored then pluralities of detectors (and possibly a plurality of sources of electromagnetic radiation) are required. This is expensive and cumbersome.

SUMMARY OF THE INVENTION

According to the present invention, at least some of the problems with the prior art are solved by means of a device having the features present in the characterising part of claim 1.

DETAILED DESCRIPTION OF EMBODIMENTS ILLUSTRATING THE INVENTION

Figure 1:
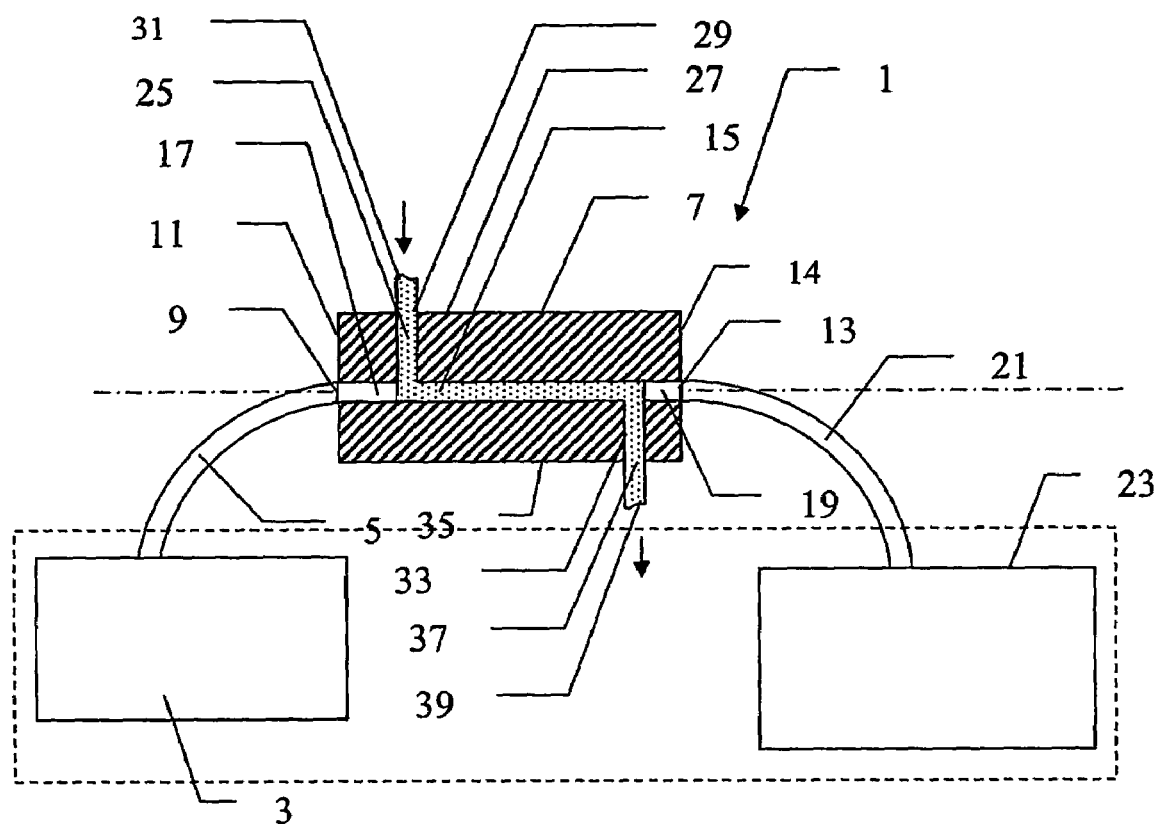
FIG. 1 shows schematically a prior art UV-detector system for detecting substances from a single source.

A prior art UV-detector system is shown schematically in FIG. 1. The system 1 comprises a UV light source means 3 with an UV-light source outward light guide 5 which is connectable to a sample-containing unit such as flow cell 7. Flow cell 7, which is in the shape of a rectangular prism with two short ends 11, 14 and four long sides, has a UV-light inlet port 9 (connectable to light guide 5) on one end 11 and a UV-light outlet port 13 on the opposite end 14. UV-light inlet port 9 and UV-light outlet port 13 are connected by a detection conduit 15 which acts as a UV-light wave-guide. Detection conduit is provided at each end with low light-loss fittings and seals 17, 19, known from the prior art and which are not shown in detail. UV-light outlet port 13 is connectable to a UV-light detector means 23 either directly, or, as shown here, by a UV-detector return light guide 21 which is connectable between UV-light outlet port 13 and UV-light detector means 23. UV-light source means 3 and UV-light detector means 23 may be combined in a single unit as represented by a box with dashed lines. A combined UV-light source means and UV-detector means called "Monitor UV-900" is available from Amersham Biosciences, Uppsala, Sweden. In use, UV light emitted from UV light source means 3 is transmitted to UV-light detector 23 via UV-light source outward light guide 5, fittings and seal 17, detection conduit 15, seal 19 and UV-detector return light guide 21. UV-light detector means 23 produces output signals S which depend on the amount of UV-light that it detects and these signals S are transmitted to a control device (not shown). If the amount of UV-light entering detection conduit 15 is kept constant, then the amount of UV-light detected by UV-light detector means 23 depends on the amount of UV-light absorbed by UV-light absorbing sample liquids in detection conduit 15. The control device can be arranged to control devices upstream and/or downstream of the flow cell 7, in order to ensure that the liquid samples are dealt with as required by the protocol under which the system is being operated. For example, if the protocol that the system is operating under requires that all sample liquids which block a certain percentage of UV-light are to be stored as fractions in a fraction collector (not shown) and all other samples thrown away, then the control device would control a valve (not shown) to switch the flow out of the flow cell 7 to a fraction collector or to waste at the appropriate time.

The end of conduit 15 nearest to UV-light input port 9 is connected to a sample inlet conduit 25 which extends from detection conduit 15 to a long side 27 of flow cell 7. Inlet conduit 25 has an opening 29 on long side 27 and is connectable to a sample inlet tube 31 connectable to a sample source such as a liquid chromatography column or the like (not shown). The end of detection conduit 15 nearest to seal 19 is connected to a sample outlet conduit 33 which extends from conduit 15 to another long side 35 of flow cell 7. Outlet conduit 33 has an opening 37 on long side 35 and is connectable to a sample outlet tube 39 connectable to a fraction collector or the like (not shown) or a waste outlet (not shown). In use, samples can be inputted into the flow cell 7 via sample inlet tube 31 and the samples then pass though inlet conduit 21, detection conduit 15 and outlet conduit 22, before leaving the flow cell and entering sample outlet tube 39.

The UV-detector system can be used as follows:

UV-light source means 3 is activated to produce UV-light and UV-light detector means 23 is activated to receive UV-light and to produce a signal S. A source of samples such as the outlet from a chromatography column is connected to sample inlet tube 31 and sample liquids are allowed to flow through flow cell 7 at a known flow rate. Let us assume that the output from the chromatography column comprises a large liquid plug A of buffer solution which does not absorb UV-light followed by a number of smaller liquid plugs of UV-light absorbing liquid B separated by liquid plugs of buffer solution A, and finally a large liquid plug of buffer solution A. As the buffer solution does not absorb UV-light then the intensity of the UV-light detected by UV-light detector 23 will be at maximum intensity when liquid plug of buffer solution A travels through detection conduit 15. As the front end of a plug of UV-light absorbing liquid B enters detection conduit 15 from inlet conduit 25, the sample in plug B absorbs some of the UV-light and the intensity of the light received by UV-light detector 23 begins to decrease. This decrease causes the signal S from UV-light detector means 23 to decrease correspondingly. The time T1 that the change in signal S occurred at can be used by the control means to calculate the time T2 when the front end of sample plug B will reach the valve at its known flow rate, and the valve can be controlled so that sample plug B will be collected in the correct fraction collector container, or sent to the waste outlet, as desired. As more of detection conduit 15 is filled with plug B the intensity of UV-light received by UV-light detector means 23 continues to fall, until it reaches a minimum when detection conduit 15 is completely filled with plug B. The intensity of UV-light received by UV-light detector means 23 remains at the minimum until the back end of plug B and the front end of the following plug of buffer solution A enter detection conduit 15. As soon as buffer solution A begins to enter detection conduit 15, the amount of UV-light absorbed in the detection conduit 15 begins to decrease and the amount of UV-light detected by UV-light detector means 23 begins to increase. The time T3 that the change in signal S occurred at can be used by the control means to calculate the time T4 when the front end of buffer solution plug A will reach the valve at its known flow rate, and the valve can be controlled so that buffer solution A will be sent to the waste outlet or, collected in the correct fraction collector container, as desired. As soon as detection conduit 15 is completely filled with buffer solution A again, the intensity of UV-light received by UV-light detector 23 means returns to its maximum value. It remains at this value until the front end of a new sample plug B enters detection conduit 15, at which point the intensity starts to drop and the signal S from UV-light detector changes in response to this drop in UV-light intensity detected by UV-light detector means 23. This cycle can be repeated until all the samples have passed through the flow cell 7.

Figure 2:
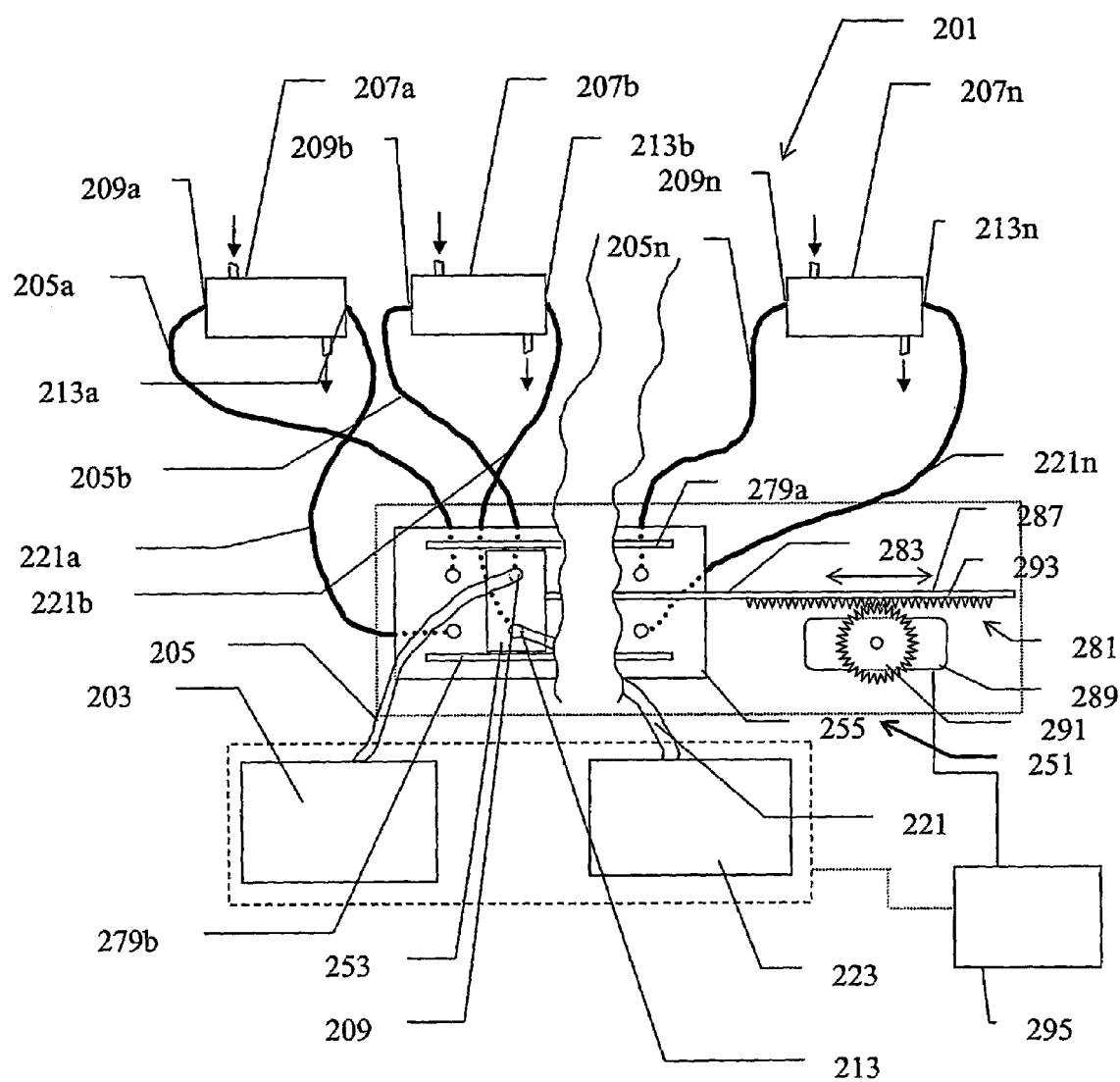
FIG. 2 shows schematically a UV-detector system for detecting substances from a plurality of sources in accordance with a first embodiment of the present invention.
Figure 3:
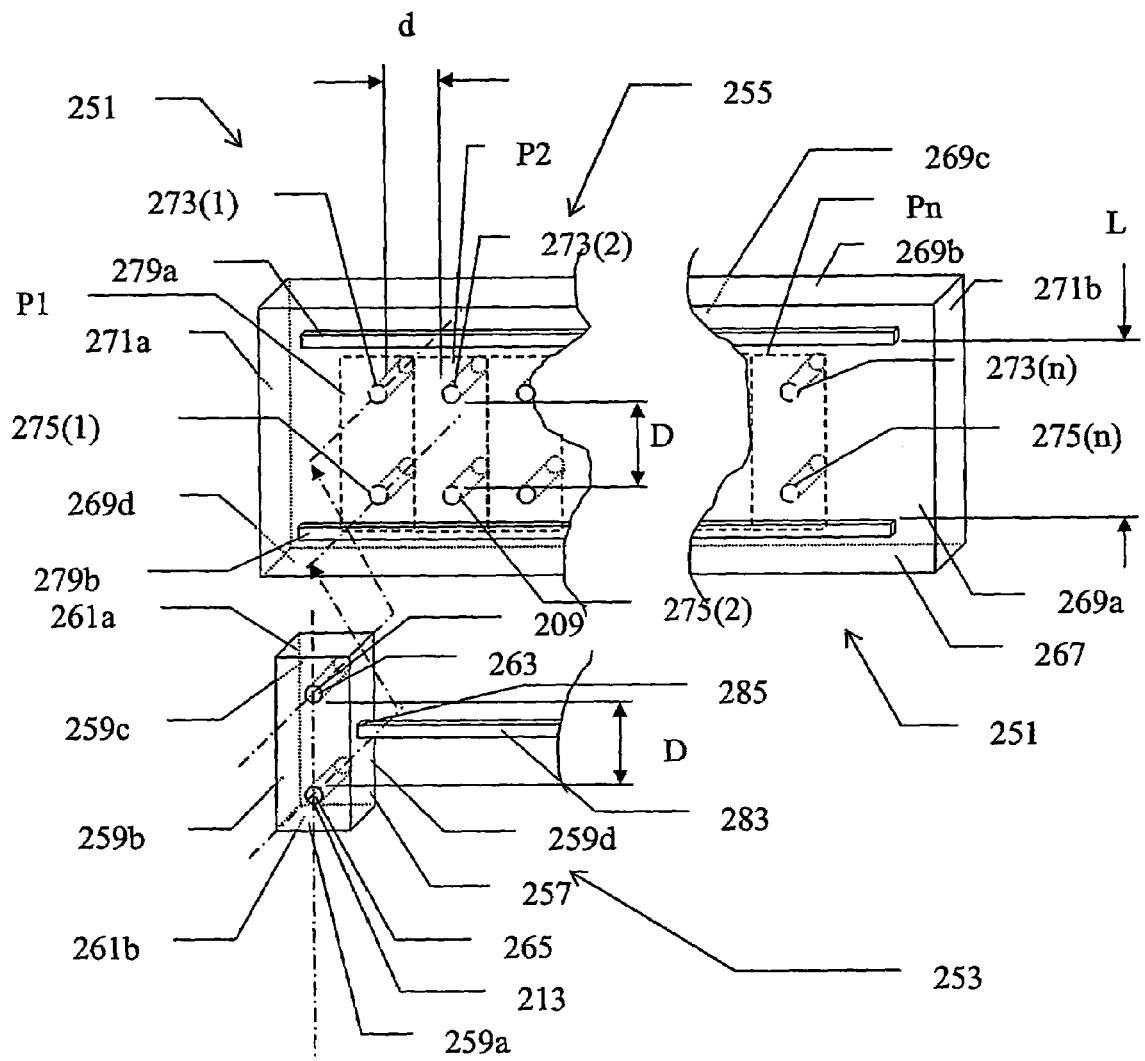
FIG. 3 shows schematically an enlargement of one embodiment of a light multiplexer in accordance with the present invention.

FIG. 2 shows schematically an embodiment of a UV-detector system 201 for detecting substances from a plurality of sources and FIG. 3 shows schematically a multiplexer 251 in accordance with a first embodiment of the present invention. In this embodiment the system comprises a plurality of sample-containing units such as flow cells 207a-207n but only one UV-light source means 203 and only one UV-light detector means 223. Each flow cell 207a-207n is provided with a respective UV-light inlet port 209a-209n connectable to a respective outward light guide 205a-205n and a respective UV-light outlet port 213a-213n connectable to a respective return light guide 221a-221n. In order for UV-light to be able to be transmitted to the flow cells 207a-207n from the single UV-light source means 203, and for UV-light to be received at the single UV-light detector means 223 from the flow cells 207a-207n, a light multiplexer 251 is provided between the flow cells 207a-207n and the UV-light source means 203 and UV-light detector means 223. Light multiplexer 251 comprises a first part in the form of a sled 253 and a second part in the form of a base 255. First part 253 and second part 255 are movable relative to each other.

As shown in more detail in FIG. 3, sled 253 comprises a rectangular prism shaped body 257 with four long sides 259a-259d of length L cm and two ends 261a, 261b. Sled 253 is provided with two parallel first outward and return through holes 263, 265 which extend through body 257 from a first long side 259a to the opposite long side 259c. First outward and return through holes 263, 265 are a distance D cm apart and are preferably positioned on the centre line of sled 253. The opening 209 of first outward through hole 263 on long side 259a is able to be connected to an outward light guide 205 connectable to UV-light source means 203 and will henceforth be called a UV-light inlet port 209. The opening 213 of first return through hole 265 on long side 259a is able to be connected to a return light guide 221 connectable to UV-light detector means 223 and will henceforth be called a UV-light outlet port 213.

Fixed base 255 comprises a rectangular prism shaped body 267 with four long sides 269a-269d and two ends 271a, 271b. Base 255 is provided with n pairs of parallel second outward and second return through holes 273(1)-273(n), respectively 275(1)-275(n), arranged in two parallel lines, and which extend through body 267 from a first long side 269a to the opposite long side 269c. Second outward and return through holes 273(1)-273(n) and 275(1)-275(n) are preferably in the form of wave guides to reduce transmission losses in them. Each pair of second outward and return through holes 273(1), 275(1), 273(2), 275(2), . . . 273(n), 275(n) is spaced apart from its neighbouring pair of second outward and return through holes by a distance d cm, and the distance between the two second outward and return through holes in each pair of second outward and return through holes is D cm. Each second outward through hole 273(1)-273(n) is connectable to its corresponding flow cell outward light guide 205a-205n leading to a flow cell 207a-207n. Each second inward through hole 275(1)-275(n) is connectable to its corresponding flow cell return light guide 221-221n leading from a flow cell 207a-207n.

First long side 269a may be provided with aligning and positioning means for the sled 253. Aligning and positioning means for the sled 253 is intended to ensure that it is possible to position the first outward and return holes 263, 265 in sled 253 in alignment with the corresponding second outward holes 273(1)-273(n) and return holes 275(1)-275(n) in fixed base 255. Aligning and positioning means for the sled 253 can comprise two parallel guide rails 279a, 279b mounted a distance L apart. Guide rails 279a, 279b are at least ((n+1)*d) cm long. They are positioned so that their ends extend beyond the ends of the two parallel rows of second outward and return through holes 273(1)-273(n), 275(1)-275(n) and are arranged at such distances from said holes that when sled 253 is placed with its ends 261a, 261b in contact with guide rails 279a, 279b and side 259c facing side 269a of body 267, then first outward through hole 263 is aligned with the plane of the row of second outward though holes 273(1)-273(n), and first return through hole 265 is aligned with the plane of the row of second return through holes 275(a)-275(n). Sled 253 is mountable between guide rails 279a, 279b by any suitable means (not shown) which allow it to move along the guide rails while holding side 259c of sled 253 close to side 269a of base 255. Preferably the gap between sled 253 and base 255 is less than 1 mm, more preferably between 0.01 and 0.02 mm, in order to reduce transmission losses. Sled 253 is attachable to an actuator 281 by means of a connecting rod 283 attached at one end 285 to side 259d and at the other end 287 to actuator 281. Actuator 281 is shown in FIG. 2 as an electric motor 289 provided with a cog wheel 291 which meshes with teeth 293 provided on connecting rod 283. Electric motor 289 is preferably an accurately controllable motor such as a stepper motor and is controllable by control means 295 such as a computer or microprocessor. Control means 295 may also control UV-light source means 203 and UV-light detector means 223. When motor 289 is rotated clockwise as shown in the figure then connecting rod 283 pulls sled to the right and when motor 289 is rotated anticlockwise connecting rod 283 pushes sled 253 to the left. Motor 289 is controllable so that sled 253 can be moved rapidly and accurately between predefined positions P1-PN on body 267. Each predefined position PX corresponds to a position where the centre axis of first outward through hole 263 is aligned with the centre axis of a second outward through hole 273(x) and the centre axis of return through hole 265 is aligned with the centre axis of a second through hole 275(x).

The system may operate as follows:

UV-light source means 203 is activated and UV-light is transmitted into light guide 205 to first outward through hole 263. Sled 253 is moved to position P1 and the UV-light passes out of first outward through hole 263 into second outward through hole 273(1). It passes out of second outward through hole 273(1) into light guide 205a which feeds it into the inlet port 209a of flow cell 207a. Flow cell 207a has a detection conduit (not shown) which feeds any UV-light that has not been absorbed in the detection conduit to outlet port 213a which introduces it into UV light detector input light guide 221a. This passes the light to second return through hole 275(1) which transmits it to first return through hole 265. This is connected to UV-light detector input light guide 221 which transmits the light to UV-light detector means 223 which produces an output signal dependent on the intensity of the UV-light that it detects. Thus in position P1, the UV-light detector means 223 produces a signal which corresponds to the UV-light absorption which is taking place in flow cell 207a. This signal can be used by control means to control the fate of liquid flowing in flow cell 207a. After a predetermined time, for example a few milliseconds or hundredths or tenths of a second, actuator 281 is activated by control means 295 to move the sled to position P2 where first outward through hole 263 is aligned with second outward through hole 273(2) and first return through hole 265 is aligned with second return hole 275(2), and UV-light detector means 223 produces a signal which corresponds to the UV-light absorption which is taking place in flow cell 207b. After a predetermined time, actuator 281 is activated to move the sled to the next position e.g. P3 and so on until the sled has been moved in steps to position Pn. After a predetermined time at position Pn, the sled is rapidly return to position P1 and then the cycle of step movements from one position Px to the adjacent position P(x+1) is repeated. In this way, the flows in each of the UV-light flow cells 207a-207n are individually sampled one after the other. The advantage of this system is that only one UV-light source means and one UV-light detector means is needed for n UV-light flow cells.

Alternatively, the sled can be moved in a first direction from a position Px to the position P(x+2) (or (x+3) or (x+4), etc.) until it reaches the last position and then it can return in the direction opposite the first direction via the positions P that it did not stop at when moving in the first direction.

In a preferred embodiment of the present invention, the actuator is a voice coil. A voice coil comprises a movable magnetic core suspended in a coil connected to a power supply. By varying the direction and strength of a current applied to the coil, the core can be made to move in backwards and forwards along the longitudinal axis of the coil and thereby act as a linear actuator. Voice coils are normally used in loud speakers to move the loudspeaker cones to generate sound and have operating frequencies of the order of 10 s of kilohertz. They accelerate and decelerate rapidly. A suitable voice coil for moving a sled is available from BTI, Kimco, Calif., USA and it can be controlled by a control circuit such as the VCA 100 from the same manufacturer. Using such an arrangement, a sled can be moved from one position Px and brought to rest in another position P(x+1) in under 5 milliseconds.

While the invention has been illustrated with an example of flow cells using UV-light, it is possible to use a multiplexer in accordance with the present invention for any type of electromagnetic radiation, in particular, visible light and IR radiation. Additionally, while the first part, i.e. the sled has been shown being moved by an actuator, it is conceivable to move the second part, i.e. the base by an actuator instead. Furthermore the second outward and return through holes do not have to be arranged as two parallel, straight rows, but may be arranged in other layouts, for example as pairs of outward and return through holes arranged in a straight line or a circle, or as two concentric circles, e.g. with the outward through holes arranged equidistantly spaced in a first circle and the return through holes equidistantly arranged in a second circle concentric with the first circle.

The above mentioned embodiments are intended to illustrate the present invention and are not intended to limit the scope of protection claimed by the following claims.

What is claimed is:

1. A liquid analysis system including a plurality of sample containing units (207a-207n) comprising a multiplexer for electromagnetic radiation, said multiplexer comprising:
   a first part (253) provided with a first outward through hole (263) connectable to a source of electromagnetic radiation (203) and a first return through hole (265) connectable to a detector of electromagnetic radiation (223), wherein said first outward through hole (263) and said first return through hole (265) are spaced a distance D apart;
   a second part (255) provided with a plurality of second outward though holes (273(1)-273(n)) and a plurality of second return through holes (275(1)-275(n)) wherein said second outward through holes (273(1)-273(n)) and said second return through holes (275(1)-275(n)) are arranged in equidistantly spaced apart pairs (273(1), 275(1); 273(2), 275(2); . . . 273(n), 275(n)) of second outward and return through holes, with each second outward hole (273(x)) at a distance D from its second return through hole (275(x)),
   wherein said first part (253) is movable relative to said second part (255) from a first position P1 in which first outward through hole (263) is aligned with a second outward through hole (273(1)) and said first return through hole (265) is aligned with a second return through hole (275(1)), to a second position Px in which first outward through hole (263) is aligned with another second outward through hole (273(x)) and said first return through hole (265) is aligned with another second return through hole (275(x)).

2. The liquid analysis system of claim 1, wherein said second outward through holes (273(l)-273(n)) and said second return through holes (275(1)-275(n)) are arranged in two parallel rows.

3. The liquid analysis system of claim 1, further comprising an actuator (281) for moving said first part (253) relative to said second part (255).

4. The liquid analysis system of claim 3, wherein said actuator comprises a voice coil.

5. The liquid analysis system of claim 3, wherein said actuator comprises an electric motor.

6. The liquid analysis system of claim 1, wherein some or all of said through holes (263, 265, 273(1)-273(n), 275(1)-275(n)) are wave guides.

7. The liquid analysis system of claim 1, wherein the second outward through hole (273(x)) in each pair of equidistantly spaced apart pairs (273(1), 275(1); 273(2), 275(2); . . . 273(n), 275(n)) of second outward and return through holes, is connectable to an inlet port (209(x)) in a sample-containing unit (207(x)) and the said second return through hole (275(x)) from the same pair of second outward and return through holes (273(x), 275(x)) is connectable to an outlet port (213(x)) in the same sample-containing unit (207(x)).

* * * * *